US008021675B2

(12) United States Patent
Graham et al.

(10) Patent No.: US 8,021,675 B2
(45) Date of Patent: *Sep. 20, 2011

(54) PESTICIDE COMPOSITIONS

(75) Inventors: Michael Clair Graham, Zionsville, IN (US); James Edward King, Carmel, IN (US); Martin Charles Logan, Indianapolis, IN (US); Dennis George Wujek, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/787,450

(22) Filed: May 26, 2010

(65) Prior Publication Data

US 2010/0234437 A1  Sep. 16, 2010

(51) Int. Cl.
    A01N 25/00    (2006.01)
    A01N 25/08    (2006.01)
    A01N 25/34    (2006.01)
    A01N 37/18    (2006.01)
    A01M 1/24     (2006.01)

(52) U.S. Cl. ............ 424/410; 424/84; 514/616; 43/124; 43/132.1

(58) Field of Classification Search .......................... None
See application file for complete search history.

(56) References Cited

U.S. PATENT DOCUMENTS

| 4,834,977 A | 5/1989 | Kohama et al. |
| 5,061,698 A * | 10/1991 | Malouf et al. .................. 514/64 |
| 5,096,710 A | 3/1992 | Minagawa et al. |
| 5,691,383 A | 11/1997 | Thoms et al. |
| 5,951,995 A * | 9/1999 | Adamoli et al. ............... 424/408 |
| 6,370,812 B1 | 4/2002 | Burns et al. |
| 6,397,516 B1 | 6/2002 | Su |
| 6,668,483 B1 | 12/2003 | Trivisani et al. |
| 6,857,223 B2 * | 2/2005 | Su ................................... 43/131 |
| 7,820,189 B2 * | 10/2010 | Graham et al. ................ 424/410 |
| 2002/0004459 A1 | 1/2002 | Adamoli, Jr. et al. |
| 2003/0014906 A1 | 1/2003 | Roe |
| 2003/0152605 A1 | 8/2003 | Martin et al. |

FOREIGN PATENT DOCUMENTS

| EP | 0431468 | 6/1991 |
| EP | 0846417 | 6/1998 |
| WO | 0062610 | 10/2000 |
| WO | 0107354 | 3/2001 |
| WO | 02052940 | 7/2002 |

OTHER PUBLICATIONS

Database CA [Online] Chemical Abstracts Service, Columbus, Ohio, US; 1888, Kohama, Takuji et al: "Organophosphate or other insecticide—containing baits for insect control": XP002580247 retrieved from STN Database accession No. 110:187821 *abstract* & JP 63 218 605 A (Arigaki Yakuhin Kogyo K. K., Japan) Sep. 12, 1988.

Database CA [Online] Chemical Abstracts Service, Columbus, Ohio, US; 1988, Takasago, Yoshiharu et al "Laminated sheets containing insectidices and fibrous materials" XP002580248 retrieved from STN.

Database WPI Week 200327 Thomson Scientific, London, GB; AN 2003-2711313 XP002580249 & JP 2002 363020 A (Takeda Chem Ind Ltd).

Database WPI Week 198928 Thomson Scientific, London, GB; AN 1989-204057 XP002580250 & JP 01 143806 A (Sumitomo Chem Ind KK).

Database WPI Week 198942 Thomson Scientific, London, GB: AN 1989-304343 XP002580251 & JP 01 224307 A (Sumitomo Chem Ind KK).

* cited by examiner

*Primary Examiner* — Shanon A Foley
(74) *Attorney, Agent, or Firm* — Carl D. Corvin

(57) ABSTRACT

This invention is related to the field of compositions useful in the control of pests that eat cellulose, such as, termites, where said composition is compacted and where said composition comprises alpha-cellulose, water, and a pesticide.

12 Claims, No Drawings

PESTICIDE COMPOSITIONS

This application claims the benefit of the following earlier filed applications, U.S. non-provisional application Ser. No. 10/594,741 which was filed on 28 Sep. 2006, which claimed the benefit of PCT/US05/10391 which was filed on 28 Mar. 2005, which claimed the benefit of U.S. provisional application 60/577,218 which was filed on 29 Mar. 2004. The contents of these earlier filed applications are hereby incorporated, by reference.

This invention is related to the field of compositions useful in the control of pests that eat cellulose, such as, termites.

Cellulose is the most abundant composition on the planet. It is a polymer that is made from glucose. Wood contains 50 weight percent cellulose and cotton contains 90 weight percent cellulose. Cellulose is a generic term for a composition that contains alpha cellulose, beta cellulose, and gamma cellulose. Alpha cellulose has a much higher degree of polymerization ("DP") than beta or gamma cellulose. Alpha Cellulose has a DP in the thousands depending on the source of the alpha cellulose. Alpha cellulose can be made into microcrystalline cellulose. Microcrystalline cellulose has a DP of less than 400.

Pests that eat cellulose are very destructive. Termites are very destructive easily causing billions of dollars in damage each year. Research is constantly being conducted to find new measures that can better control termites, especially termite species that have been difficult to control in the past.

This invention provides a solution to the problems of controlling pests that eat cellulose.

This invention is related to the field of compositions useful in the control of pests that eat cellulose, such as, termites, where said composition is compacted and where said composition comprises alpha-cellulose, water, and a pesticide.

US 2003/0152605 A1 discloses an optimum density termite composition. An optimum density was required because the applicants wanted more cellulose compacted into less volume thereby, according to the application, providing a longer term feeding composition. The composition comprises "purified cellulose" (it is not readily apparent from the application what this term means) or microcrystalline cellulose in a compacted form where the composition has a density greater than 1.033 grams per cubic centimeter. It is apparent that the applicants are not disclosing any composition that contains water in any amount. This is especially apparent when considering their problems with powder cellulose as disclosed in paragraph 0014 and their solution for deaerating the powder in paragraph 019.

Pests

Any cellulose eating pest can be controlled by the inventive compositions disclosed herein. In particular, termites can be controlled by the inventive compositions herein, especially subterranean termites such as *Reticulitermes* spp. and *Coptotermes* spp. Suitable examples of termites that can be controlled are: *Reticulitermes flavipes; Reticulitermes virginicus; Reticulitermes Hesperus; Heterotermes aureus; Coptotermes formosanus; Reticulitermes speratus; Reticulitermes grassei; Reticulitermes santonensis; Macrotermes gilvus;* and *Reticulitermes hageni.*

Alpha Cellulose

Alpha cellulose is readily available. It can be purchased from a variety of sources. One particular source is International Fiber Corporation. It is particularly preferred if the alpha cellulose is in powdered form.

Pesticides

Examples of suitable insecticides that may be used are:

(a) Pyrethroids, such as permethrin, cypemethrin, fenvalerate, esfenvalerate, deltamethrin, cyhalothrin, lambda-cyhalothrin, gamma-cyhalothrin, bifenthrin, fenpropathrin, cyfluthrin, tefluthrin, fish safe pyrethroids (for example ethofenprox), natural pyrethrin, tetramethrin, s-bioallethrin, fenfluthrin, prallethrin, 5-benzyl-3-furylmethyl-(E)-(1R,3S)-2,2-dimethyl-3-(2-oxothiolan-3-ylidenemethyl) cyclopropane carboxylate, or any of their insecticidally active isomers;

(b) Organophosphates, such as, methidathion, chlorpyrifos-methyl, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, chlorpyrifos-methyl, phosalone, terbufos, fensulfothion, fonofos, phorate, phoxim, pirimiphos-methyl, pirimiphos-ethyl, fenitrothion, fosthiazate or diazinon;

(c) Carbamates (including aryl carbamates), such as fenoxycarb, alanycarb, pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

(d) Benzoyl ureas, such as lufenuron, novaluron, noviflumuron, teflubenzuron, diflubenzuron, triflumuron, hexaflumuron, flufenoxuron or chlorfluazuron;

(e) Organic tin compounds, such as cyhexatin, fenbutatin oxide or azocyclotin;

(f) Pyrazoles, such as tolfenpyrad, pyridaben, tebufenpyrad and fenpyroximate;

(g) Macrolides, such as avermectins or milbemycins, for example abamectin, emamectin benzoate, ivermectin, milbemycin, spinosad or azadirachtin;

(h) Hormones or pheromones;

(i) Organochlorine compounds such as endosulfan, benzene hexachloride, DDT, chlordane or dieldrin;

(j) Amidines, such as chlordimeform or amitraz;

(k) Chloronicotinyl compounds such as diofenolan, clothianidin, thiacloprid, imidacloprid, thiacloprid, acetamiprid, nitenpyram or thiamethoxam;

(l) Diacylhydrazines, such as halofenozide, tebufenozide, chromafenozide or methoxyfenozide;

(m) Diphenyl ethers, such as diofenolan or pyriproxifen;

(n) Indoxacarb;

(o) Chlorfenapyr;

(p) Pymetrozine;

(q) Diafenthiuron;

(r) Toxins of microbial origin such as *B.acillus thuringiensis* endo- or exotoxins;

(s) Phenylpyrazoles such as fipronil, vanilliprole, etiprole or acetoprole;

(t) Pyridalyl; or (v) hydramethylnon

In addition to the major pesticides listed above, other pesticides having particular targets may be employed if appropriate for the intended utility of the inventive composition. Alternatively, insecticides, or acaricides, specific for particular insect species/stages may also be included in the inventive compositions (for example acaricidal ovo-larvicides, such as clofentezine, flubenzimine, hexythiazox or tetradifon; acaricidal motilicides, such as dicofol or propargite; acaricides, such as acequinocyl, fenazaquin, spirodiclofen, etoxazole, bromopropylate or chlorobenzilate; or growth regulators, such as cyromazine, methoprene, chlorfluazuron or diflubenzuron).

Examples of suitable insecticide synergists that may be used as a further active ingredient in the inventive compositions include piperonyl butoxide, sesamex, safroxan and dodecyl imidazole.

Specific examples of preferred pesticides are thiamethoxam, abamectin, emamectin benzoate, spinosad, chlorpyrifos, chlorpyrifos-methyl, profenofos, lufenuron, indoxacarb, lambda-cyhalothrin, pymetrozine, pirimicarb, methidathion, imidacloprid, acetamiprid, thiacloprid, fipronil, methoxyfenozide, chlorfenapyr, pyridaben, novaluron, noviflumuron, pyridalyl, propargite and piperonyl butoxide.

Mixtures of pesticides are also useful and many of the above can be synergistically used together.

However, it is most preferred to use a slow acting pesticide, especially with termites, so that the termites can take the pesticide, or pesticides, back to their colony and poison other colony members.

Preparation and Use

In general the amount of alpha cellulose and water to use is not critical and can vary by a wide amount depending on the other components (such as pesticide(s), binder(s), attractant(s), etc.) added to mixture of alpha cellulose and water. It is preferred that the mixture of alpha cellulose, water, and the other components, if any, upon compacting, have a density greater than 1 gram per cubic centimeter. Densities less than 1 gram per cubic centimeter can be used but are not preferable in most cases. Suitable ranges for alpha cellulose and water are in Table 1.

TABLE 1

| | Weight Percent (based on total weight of both components) | | |
|---|---|---|---|
| Component | Preferred Range | More Preferred Range | Most Preferred Range |
| Alpha Cellulose | 60 to 99 | 65 to 95 | 70 to 90 |
| Water | 40 to 1 | 35 to 5 | 30 to 10 |

In general the amount of pesticide to use is also not critical. Amounts from 0.0001 to 10 weight percent based on the weight of the inventive composition can be used (that is, alpha cellulose, water, pesticide, plus any other components desired).

The compacted composition of alpha cellulose, water, pesticide, plus any other components desired can take any useful form. A useful form is a form that the desired pest can eat. Such forms are tablets, briquettes, pellets, granules, etc. These types of forms can be made by any process known in the art. In general, more water is needed to form good pellets and less water is needed to form good briquettes.

In an unexpected and surprising manner, it has been discovered that termites that have in the past been difficult to control with baits, feed especially well upon briquettes as opposed to pellets or tablets, possibly because the briquettes of this invention can absorb liquids more easily. Consequently, it is preferred to compact the inventive composition in the shape of a briquette. One machine that can do this process is Komarek model B-100-A two roll mill available from K. R. Komarek Inc., 1825 Estes Ave., Elk Grove Village, Ill. 60007.

Once the inventive composition has been compacted, such as into briquettes, it is preferred to dry the briquettes. This drying can occur in any manner known in the art that will remove a portion of the water. This may seem paradoxical, in that it is desirable to have water in the compacted composition. After all, water is desired by cellulose eating pests, especially termites. However, while water is removed from the compacted composition it is not entirely removed from the compacted composition. At least a portion of the water that is removed from the compacted composition leaves voids in the compacted composition.

The compacted composition can then be used as a bait to control cellulose eating pests, such as subterranean termites. Many methods are known to bait such pests. In a preferred embodiment of the invention the compacted composition is placed in the ground, perhaps inside another tube that allows access for termites, and prior to placing the compacted composition in the ground or tube, or leaving it in the ground or tube, additional liquid (such as water, or a mixture of water and sugar, or a mixture of water, sugar, and salts) is contacted with the compacted composition. This method can attract even more termites to the now moistened, compacted composition, causing more feeding and more pesticide delivery to the termites and the colony. Since the compacted composition was first dried before being moisten the liquid can readily fill any voids left behind by the drying of the compacted composition.

Optional ingredients to include in the inventive composition include, but are not limited to, a preservative to retard fungal growth, and a protectant such as a bittering agent to provide a safety factor for exposed bait.

An attractant is defined as any substance or combination of substances which will lure pests. Examples of attractants are carbon dioxide and terpenes.

Feeding stimulants that can be used in the inventive composition are, for example, sugar, such as powdered sucrose, high fructose corn syrup, polyhydroxy alcohols such as glycerin, and starch.

Examples of preservatives useful in the present invention are 1,2-benzisothiazolin-3-one (PROXEL GXL®, Avecia Inc. Wilmington, Del. 19850) methyl paraben (p-hydroxybenzoic acid methyl ester) and propyl paraben (n-propyl p-hydroxybenzoate). Other known fungistats would also be effective in increasing the longevity of the bait and retarding mold growth.

The headings used herein are meant to be as a guide and are not to be used to interpret the scope of the invention.

EXAMPLES

These examples are provided to illustrate the invention. They are not to be used for limiting the scope of the invention.

Example A

Preparation of Pesticide Concentrate

| Pesticide Concentrate Table | |
|---|---|
| Wt % | Ingredient |
| 50.5 | Noviflumuron |
| 38.1 | Water |
| 10.4 | Pluronic P-104 |
| 0.7 | Proxel GXL |
| 0.3 | Antifoam B |

A pesticide concentrate containing the amounts of materials in the pesticide concentrate table was prepared as follows.

Pluronic P-104 and water were mixed together to form a solution containing 23.3 weight percent Pluronic P-104 based on the total weight of the mixture ("First Mixture"). The Pesticide concentrate was made by mixing together the First Mixture, the noviflumuron, the Proxel GXL, and the Antifoam B in the amounts required to achieve the indicated weight percents.

Example 1-A

Preparation of a Preferred Embodiment

In this example, a preferred embodiment of the inventive compositions disclosed herein is made.

Ninety kg of cellulose (BH-100 from International Fiber Corporation) was weighed into a blender. A first mixture of pesticide concentrate (see Example A) with water (1 part pesticide concentrate: 3 parts water) was then sprayed into the blender. Upon mixing, this produced a second mixture containing 0.5 weight percent pesticide, 9.2 weight percent water, and 90.3 weight percent cellulose, based on the weight of the second mixture.

Additional water was sprayed into the blender to produce a third mixture that could be compacted into briquettes. The third mixture contained 0.4 weight percent pesticide, 27.9 weight percent water, and 71.7 weight percent cellulose, based on the weight of the third mixture.

The third mixture was then fed into a compaction device. The compaction device was the Komarek briquetter, model B-100-A two-roll machine. The machine was run under the following conditions to produce briquettes: a compaction force of 1,300 kg/cm$^2$; a feed rate of 400-500 g/min; and a tip speed of 5 feet per minute.

The briquettes coming off the compaction device were then screened with a vibratory screener. The material that passed through a 4-mesh screen (4,750 micron size) was collected for recycling to the feed.

The briquettes were then dried to remove a portion of the water.

Example 1-B

Preparation of Another Preferred Embodiment

In this example, a preferred embodiment of the inventive compositions disclosed herein is made.

68.18 kg of cellulose (BH-100 from International Fiber Corporation) was weighed into a blender. A first mixture of pesticide concentrate (see Example A) with water (0.698 kg pesticide concentrate and 2.116 kg water) was then mixed into the blender. An additional 24.3 kg of water was then added to the blender. After thorough mixing, the mixture was fed into a model CL-2 California Pellet mill to produce 3/16" diameter pellets. 500-600 grams per minute of wet pellets were produced at a rotational speed of 620 feet per min. The material coming off the pellet mill was screened. Product that passed through a 4-mesh screen (4,750μ) was disposed. The pellets were dried to remove a portion of the water.

Example 1-C

Preparation of Another Preferred Embodiment

In this example, a preferred embodiment of the inventive compositions disclosed herein is made.

90.91 kg of cellulose (BH-100 from International Fiber Corporation) was weighed into a blender. 16.243 kg of BF-20 starch (From Grain Processing Corporation) was then mixed into the blender. A first mixture of pesticide concentrate (see Example A) with water (1.1 kg pesticide concentrate and 3.3 kg water) was then mixed into the blender. An additional 30.419 kg of water was then added to the blender. After thorough mixing, the mixture was fed into a model CL-2 California Pellet mill to produce 3/16" diameter pellets. 400-600 grams per minute of wet pellets were produced at a rotational speed of 620 feet per min. The material coming off the pellet mill was screened. Product that passed through a 4-mesh screen (4,750μ) was disposed. The pellets were dried to remove a portion of the water.

Example 2

Importance of Moist Baits

This example shows the importance of moisture to termites.

The moist bait was prepared in accordance with Example 1-B. Additional water was added to the bait as indicated (either 0.43 ml/g; 0.85 ml/g; 0r 2 ml/g; water/gram of bait)

The dry bait was prepared in accordance with Example 1-B. However no additional water was added.

A one-way pair choice testing environment was used. The termites were placed in a harborage and a tube allowed them a passage to the food environment. In the food environment, the termites were given a choice of two different food sources. The termites were allowed to feed on the food choices for 7 days. Between 4 and 12 reps were performed and each rep had 100-200 termite workers. Bait consumption was measured as the difference between the pre-weight and the post weight.

At 0.43 ml/g *R. flavipes, R. speratus, C. gestrol/travians*, and *H. aureus* preferred the moist bait over the dry bait. The only other species tested had no preference *R. hesperus*.

At 0.85 ml/g *R. speratus, C. gestrol/travians, H. aureus, R. grassei, C. formosanus*, and *R. virginicus* preferred the moist bait over the dry bait. *R. flavipes* and *R. hesperus* showed no preference.

At 2 ml/g *R. speratus*, and *C. gestrol/travians* preferred the moist bait over the dry bait. *R. flavipes, R. hesperus, H. aureus* showed no preference. *R. grassei* actually preferred the dry bait over the moist bait.

This example shows the importance of moisture to termite feeding, and hence to the importance of the inventive composition's ability to absorb moisture.

We claim:

1. A process to make a termite bait said process consisting essentially of the following steps:
    (a) mixing alpha-cellulose, water, and a pesticide to form a mixture; followed by
    (b) compacting said mixture to a density greater than 1 gram per cubic centimeter to form a compacted composition; followed by
    (c) drying said compacted composition to remove at least a portion of said water to produce voids in said compacted composition;
    wherein the composition after step (c) has from 60 to 99 weight percent alpha-cellulose and 40 to 1 weight percent water based on the weight of said alpha-cellulose and said water, and furthermore the composition after step (c) has from 0.0001 to 10 weight percent pesticide based on the weight of said alpha-cellulose, said water, and said pesticide and
    wherein said pesticide is selected from permethrin, cypemethrin, fenvalerate, esfenvalerate, deltamethrin, cyhalothrin, lambda-cyhalothrin, gamma-cyhalothrin, bifenthrin, fenpropathrin, cyfluthrin, tefluthrin, ethofenprox, natural pyrethrin, tetramethrin, s-bioallethrin, fenfluthrin, prallethrin, 5-benzyl-3-furylmethyl-(E)-(1R,3 S)-2,2-dimethyl-3-(2-oxothiolan-3-ylidenemethyl) cyclopropane carboxylate, methidathion, chlorpyrifos-methyl, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, chlorpyrifos-methyl, phosalone, terbufos, fensulfothion, fonofos, phorate, phoxim, pirimiphos-methyl, pirimiphos-ethyl, fenitrothion, fosthiazate diazinon, fenoxycarb, alanycarb, pirimicarb, triazamate, cloethocarb, carbofuran, furathiocarb, ethiofencarb, aldicarb, thiofurox, carbosulfan, bendiocarb, fenobucarb, propoxur, methomyl, oxamyl, lufenuron, novaluron, noviflumuron, teflubenzuron, diflubenzuron, triflumuron, hexaflumuron, flufenoxuron, chlorfluazuron, cyhexatin, fenbutatin oxide, azocyclotin, tolfenpyrad, pyridaben, tebufenpyrad, fenpyroximate, abamectin, emamectin benzoate, ivermectin, milbemycin, spinosad, azadirachtin, endosulfan, benzene hexachloride, DDT, chlordane, dieldrin, chlordimeform, amitraz, diofenolan, clothianidin, thiacloprid, imidacloprid, thiacloprid, acetamiprid, nitenpyram, thiamethoxam, halofenozide, tebufenozide, chromafenozide, methoxyfenozide, diofenolan, pyriproxifen, indoxacarb, chlorfenapyr, pymetrozine, diafenthiuron, fipronil, vanilliprole, etiprole, acetoprole, pyridalyl, or hydramethylnon.

2. A process according to claim 1 wherein said pesticide is noviflumuron or hexaflumuron.

3. A process according to claim 2 wherein the composition after step (c) has from 65 to 95 weight percent alpha-cellulose and 35 to 5 weight percent water based on the weight of said alpha-cellulose and said water.

4. A process according to claim 3 wherein the composition after step (c) has from 70 to 90 weight percent alpha-cellulose and 30 to 10 weight percent water based on the weight of said alpha-cellulose and said water.

5. A process according to claim 1, 2, 3, or 4 wherein the composition after step (c) is in the form of a briquette.

6. A composition produced after step (c) according to claim 1, 2, 3, or 4.

7. A process consisting essentially of controlling termites by placing a termite bait in the ground wherein said termite bait is made in accordance with claim 1, 2, 3, or 4.

8. A process according to claim 7 wherein said termite bait is placed inside a tube wherein said tube allows access for termites.

9. A process according to claim 7 wherein prior to placing said termite bait in the ground, said termite bait is contacted with a liquid comprising water, sugar, and optionally salt.

10. A process according to claim 8 wherein prior to placing said termite bait inside a tube, said termite bait is contacted with a liquid comprising water, sugar, and optionally salt.

11. A process according to claim 7 wherein after placing said termite bait in the ground, said termite bait is contacted with a liquid comprising water, sugar, and optionally salt.

12. A process according to claim 8 wherein after placing said termite bait inside a tube, said termite bait is contacted with a liquid comprising water, sugar, and optionally salt.

* * * * *